United States Patent [19]

Reifenberg

[11] 4,148,814

[45] Apr. 10, 1979

[54] PROCESS FOR PREPARING MONOHYDROCARBYLTIN TRIHALIDES

[75] Inventor: Gerald H. Reifenberg, Hightstown, N.J.

[73] Assignee: Pennwalt Corporation, Philadelphia, Pa.

[21] Appl. No.: 828,579

[22] Filed: Aug. 29, 1977

[51] Int. Cl.$^2$ .............................................. C07F 7/22
[52] U.S. Cl. .................................................. 260/429.7
[58] Field of Search ...................................... 260/429.7

[56] References Cited

U.S. PATENT DOCUMENTS

| | | | |
|---|---|---|---|
| 3,311,648 | 3/1967 | Herbstman et al. | 260/429.7 |
| 3,400,141 | 9/1968 | Hoye et al. | 260/429.7 |
| 3,415,857 | 12/1968 | Hoye | 260/429.7 |
| 3,426,046 | 2/1969 | Hatch | 260/348 |
| 3,442,912 | 5/1969 | Hatch | 260/348 |
| 3,454,610 | 7/1969 | Langer | 260/429.7 |
| 3,459,779 | 8/1969 | Newmann | 260/429.7 |
| 3,462,462 | 8/1969 | Hatch | 260/348 |
| 3,651,108 | 3/1972 | Giannaccari et al. | 260/429.7 |
| 3,862,198 | 1/1975 | Kugele et al. | 260/429.7 |
| 3,971,817 | 9/1976 | Jung et al. | 260/429.7 |

OTHER PUBLICATIONS

Price et al., Sulfur Bonding, The Ronald Press Co. N.Y., pp. 152, 153, 160, 161 (1962).
Johnson, Ylid Chemistry, Academic Press, N. Y., p. 17 (1966).
Reid, Organic Chemistry of Bivalent Sulfur, Chemical Publ. Co., N.Y., V1, pp. 32 and 33 (1958).

*Primary Examiner*—Helen M. S. Sneed
*Attorney, Agent, or Firm*—Robert G. Danehower

[57] ABSTRACT

A process is provided for preparing monohydrocarbyltin trihalides, $RSnX_3$, wherein R is an alkyl, cycloalkyl, alkaryl, aryl or aralkyl group of 1–24 carbon atoms, and X is a halogen atom by the redistribution reaction between a tetrahydrocarbyltin, $R_4Sn$, a trihydrocarbyltin halide, $R_3SnX$, or a dihydrocarbyltin dihalide, $R_2SnX_2$, and a tin tetrahalide, $SnX_4$, in the presence of sulfonium or isothiuronium salts as catalysts.

9 Claims, No Drawings

PROCESS FOR PREPARING MONOHYDROCARBYLTIN TRIHALIDES

BACKGROUND OF THE INVENTION

The redistribution reaction between tetraalkyltins, tetraaryltins, and alkyl- and aryltin halides with tin tetrahalides to form monohydrocarbyltin trihalides, is well-known. See R. K. Ingham, et al., *Chem. Rev.*, 60, 459 (1960).

This reaction is represented by the following equations:

$$R_4Sn + 3SnX_4 \rightarrow 4RSnX_3 \quad (1)$$

$$R_3SnX + 2SnX_4 \rightarrow 3RSnX_3 \quad (2)$$

$$R_2SnX_2 + SnX_4 \rightarrow 2RSnX_3 \quad (3)$$

In these equations R is a hydrocarbyl group of 1 to 24 carbons and X is halogen.

Neumann et al. in Angew. *Chem. Internat. Ed.*, Vol. 2 (No. 4), 165 (1963) have shown that reactions (1) and (2) are actually the sum of two or more consecutive reactions (equations 4 to 6).

$$R_4Sn + SnX_4 \rightarrow R_3SnX + RSnX_3 \quad (4)$$

$$R_3SnX + SnX_4 \rightarrow R_2SnX_2 + RSnX_3 \quad (5)$$

$$R_2SnX_2 + SnX_4 \rightarrow 2RSnX_3 \quad (6)$$

It can be seen that equation 1 is the sum of equations 4–6 and equation 2 is the sum of equations 5 and 6. When R is aryl, reactions 4 to 6 proceed readily and without a catalyst. On the other hand, if R is alkyl, only reactions 4 and 5 proceed readily uncatalyzed. The difficulty of converting a dialkyltin dihalide to a monoalkyltin trihalide in the absence of catalysts (equation 3 or 6) is the reason why the conversion of tetraalkyltins or trialkyltin halides to monoalkyltin trihalides (equations 1 and 2) does not proceed to completion. Thus, Grant and Van Wazer, *J. Organometal. Chem.*, Vol. 4, 229 (1965) report that only a 71% conversion (based on analysis) of dimethyltin dichloride was obtained in 17 hours when it reacted with tin tetrachloride to form monomethyltin trichloride.

Langer, in U.S. Pat. No. 3,454,610, shows that a greater than 90% yield of monomethyltin trichloride - dimethylsulfoxide complex is obtained by reacting dimethyltin dichloride with tin tetrachloride in dimethyl sulfoxide solvent according to equation 6, but the process requires large quantities of solvent and the cost of freeing the monomethyltin trichloride from the complex is high.

Neumann, in U.S. Pat. No. 3,459,779, discloses the preparation of monoalkyltin trihalides from dialkyltin dihalides and tin tetrahalides by using large amounts of phosphorus oxychloride or preferably, a mixture of phosphorus oxychloride and phosphorus pentoxide as catalysts.

Recently, Kugele and Parker, U.S. Pat. No. 3,862,198, have shown that quarternary ammonium, phosphonium, or arsonium salts catalyze the conversion of dialkyltin dihalides to monoalkyltin trihalides with tin tetrahalides. The yields ranged from poor to excellent depending on the nature of the dialkyltin dihalide.

DETAILED DESCRIPTION OF THE INVENTION

I have now discovered that increased yields of monohydrocarbyltin trihalides in relatively short periods of time can be achieved by carrying out reactions (1), (2), or (3) in the presence of sulfonium or isothiuronium salts as catalysts. The mole ratios employed are substantially as shown in equations 1, 2 and 3 above. Slight deviations in mole ratios can be made without serious adverse effects.

Examples of tin tetrahalide reactants that can be used are tin tetrachloride, tin tetrabromide and tin tetraiodide. The preferred tin tetrahalide is tin tetrachloride because it is the least expensive.

Tin tetrabromide, tin tetrachloride, and tin tetraiodide can be prepared by the direct halogenation of tin in a liquid reaction medium provided by the liquid reaction product.

The hydrocarbyltin reactants in my process are $R_4Sn$, $R_3SnX$ and $R_2SnX_2$ in which R is a hydrocarbyl group and X is halogen including bromide, chloride and iodide. The hydrocarbyl group will vary within the range of $C_1$ to $C_{24}$ carbon content. Preferably, the carbon content will be within the range of $C_1$ to $C_{12}$ carbons. The hydrocarbyl group includes alkyl, aryl, alkaryl, aralkyl and cycloalkyl groups. These groups can be saturated or unsaturated and they can be substituted with inert substituents such as ethers, alcohols, halides and esters.

Hydrocarbyltin starting materials that can be used are tetramethyltin, tetraethyltin, tetra (n-butyltin), tetraamyltin, tetra (n-octyl) tin, tetra (isooctyl) tin, tetra(2-ethylhexyl)tin, tetra(n-propyl)tin, tetra(isopropyl)tin, trimethyltin chloride, trimethyltin bromide, trimethyltin iodide, triethyltin chloride, triethyltin bromide, triethyltin iodide, tri n-propyltin chloride, tri n-propyltin bromide, tri n-propyltin iodide, tri n-butyltin chloride, tri n-butyltin bromide, tri n-butyltin iodide, tri sec-butyltin chloride, tri-isobutyltin bromide, tri n-octyltin chloride, tri n-octyltin bromide, tri n-octyltin iodide, tri isooctyltin chloride, tri isooctyltin bromide, tri isoctyltin iodide, tri 2-ethylhexyltin chloride, tri 2-ethylhexyltin bromide, tri 2-ethylhexyltin iodide, dimethyltin dichloride, dimethyltin dibromide, dimethyltin diiodide, diethyltin dichloride, diethyltin dibromide, diethyltin diiodide, di-n-propyltin dichloride, di-n-propyltin dibromide, di-n-propyltin diiodide, diisopropyltin dichloride, di-n-butyltin dichloride, di-n-butyltin dibromide, di-n-butyltin diiodide, diisobutyltin dichloride, di-sec-butyltin dichloride, di-sec-butyltin dibromide, diamyltin dichloride, dihexyltin dichloride, diheptyltin dichloride, di-n-octyltin dichloride, di-n-octyltin dibromide, di-n-octyltin diiodide, diisooctyltin dichloride, diisooctyltin dibromide, diisooctyltin diiodide, di-2-ethylhexyltin dichloride, di-2-ethylhexyltin dibromide and di-2-ethylhexyltin diiodide, di(dodecyltin) dichloride, di (dodecyltin) dibromide, tetrakis (dodecyl) tin, tris (dodecyl)tin chloride, tris(dodecyl)tin iodide, tetraphenyltin, triphenyltin chloride, triphenyltin bromide, triphenyltin iodide, diphenyltin dichloride, diphenyltin dibromide, diphenyltin diiodide, tribenzyltin chloride, tribenzyltin bromide, tribenzyltin iodide, tetrabenzyltin, dibenzyltin dichloride, dibenzyltin dibromide, dibenzyltin diiodide, tricyclohexyltin chloride, dicyclohexyltin dichloride, dicyclohexyltin dibromide, di(p-tolyltin) dichloride, tri(p-tolyltin) chloride, tetra p-tolyltin.

Preferred hydrocarbyltins are the dialkyltin dichlorides and most preferably the dialkyltin dichlorides with hydrocarbon radicals of 1-8 carbon atoms.

The hydrocarbyltin compounds can be obtained commercially from M and T Chemicals Incorporated. The hydrocarbyltin compounds can be prepared by Grignard - type processes as shown in U.S. Pat. No. 2,675,398 and U.S. Pat. No. 2,959,596 or alkyl chlorides can be reacted directly with molten tin metal to yield dialkyltin dichloride as shown in U.S. Pat. No. 2,679,506. These patents are incorporated herein by reference. In another process, tin tetrachloride can be alkylated or arylated by reactive metal alkyl compounds of aluminum, sodium and lithium.

The products that can be prepared by my process include methyltin trichloride, methyltin tribromide, methyltin triiodide, ethyltin trichloride, ethyltin tribromide, ethyltin triiodide, n-propyltin trichloride, n-propyltin tribromide, n-propyltin triiodide, isopropyltin trichloride, n-butyltin trichloride, n-butyltin tribromide, n-butyltin triiodide, isobutyltin trichloride, sec-butyltin trichloride, sec-butyltin triiodide, n-amyltin trichloride, n-hexyltin trichloride, n-heptyltin trichloride, n-octyltin trichloride, n-octyltin tribromide, n-octyltin triiodide, isooctyltin trichloride, isooctyltin tribromide, isooctyltin triiodide, 2-ethylhexyltin trichloride, 2-ethylhexyltin tribromide, 2-ethylhexyltin triiodide, dodecyltin trichloride, dodecyltin tribromide, dodecyltin triiodide, phenyltin trichloride, phenyltin tribromide, phenyltin triiodide, cyclohexyltin trichloride, benzyltin trichloride, benzyltin tribromide, benzyltin triiodide, p-tolyltin trichloride.

The polyhydrocarbyltin compound is reacted with the tin tetrahalide in the stoichiometry substantially as indicated by reactions (1), (2), and (3) above in the presence of a catalyst as described below:

Sulfonium and isothiuronium salt catalysts which are operable in my invention are represented by the following:

phenylpropylsulfonium iodide, dimethyl-o-ethylphenylsulfonium chloride, dimethylethylsulfonium nitrate, dimethylbenzylsulfonium acetate, methylethylpropylsulfonium p-toluenesulfonate, dimethylisopropylsulfonium tribromostannite, dimethyl t-butyl-sulfonium triiodostannite, methylethylcyclohexylsulfonium iodide, dibenzylallylsulfonium methosulfate, tris(dimethylbenzylsulfonium)phosphate, dimethyltolylsulfonium acetate, tetramethylenemethylsulfonium nitrate, tetramethylenemethylsulfonium chloride, tetramethylenemethylsulfonium iodide, tetramethylenemethylsulfonium methosulfate, pentamethylenebutylsulfonium iodide, S-methylisothiuronium chloride, S-methylisothiuronium bromide, S-methylisothiuronium iodide, S-butylisothiuronium iodide, S-ethylisothiuronium iodide, S-t-butylisothiuronium methosulfate, bis(S-octylisothiuronium)sulfate, tris(S-benzylisothiuronium)phosphate, S-cyclohexylisothiuronium acetate, S-alkylisothiuronium nitrate, S-$\beta$-phenylethylisothiuronium trichlorostannite, N,N,N$^1$,N$^1$ -S-pentamethylisothiuronium iodide, N,N,N$^1$,N$^1$ -tetraphenyl-S-benzylisothiuronium nitrate, N-ethyl-S-propylisothiuronium acetate, N,N$^1$-diphenyl-S-2-ethylhexylisothiuronium iodide, N,N-dimethyl-N$^1$,N$^1$-diethyl-S-butylisothiuronium chloride, and N,N,N$^1$,N$^1$ -tetramethyl-S-isopropylisothiuronium p-toluenesulfonate.

Preferred catalysts are the chloride, bromide, or iodide salts of trimethylsulfonium, tetramethylenemethylsulfonium, S-benzylisothiuronium, S-methylisothiuronium, S-ethylisothiuronium, S-butylisothiuronium cations. The most preferred anion is chloride (from a cost standpoint) and the most preferred cation is trimethylsulfonium (from an activity standpoint).

The amount of catalyst required will be at least about 0.001 mole per mole of hydrocarbyltin starting material. Preferably, the amount of catalyst employed will range from about 0.001 to 0.5 mole per mole of hydrocarbyltin starting material. As the amount of catalyst is increased, the reaction rate increases. Normally, the catalyst is

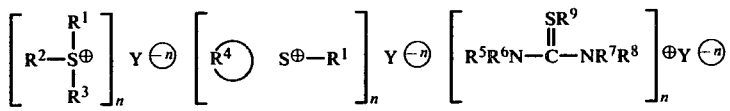

wherein:

R$^1$, R$^2$, R$^3$, R$^5$, R$^6$, R$^7$, R$^8$, and R$^9$ are hydrocarbyl radicals including alkyl, aryl, aralkyl, alkaryl, or cycloalkyl of 1-24 carbon atoms. The hydrocarbyl radicals may be saturated or unsaturated. They may also contain inert substituents such as ethers, halides, alcohols and esters. R$^5$, R$^6$, R$^7$, and R$^8$ can also be hydrogen.

R$^4$ is a hydrocarbon linking group of 3-5 carbon atoms; n is the valence of the anion Y; and, Y is an anion such as Cl$^{-1}$, Br$^{-1}$, I$^{-1}$, SO$_4^{-2}$, CH$_3$SO$_4^{-1}$, p-CH$_3$C$_6$H$_4$SO$_3^{-1}$, p-BrC$_6$H$_4$SO$_3^{-1}$, PO$_4^{-3}$, NO$_3^{-1}$, CH$_3$CO$_2^{-1}$, SnCl$_3^{-1}$, SnBr$_3^{-1}$, and SnI$_3^{-1}$. Generally, n will be 1 or 2.

Examples of catalysts are trimethylsulfonium chloride, trimethylsulfonium bromide, trimethylsulfonium iodide, trimethylsulfonium methosulfate, bis(trimethylsulfonium)sulfate, tris(trimethylsulfonium)phosphate, trimethylsulfonium nitrate, trimethylsulfonium acetate, trimethylsulfonium trichlorostannite, triethylsulfonium iodide, tributylsulfonium bromide, tridodecylsulfonium p-bromobenzesulfonate, trioctadecylsulfonium methosulfate, tribenzylsulfonium iodide, triphenylsulfonium chloride, dimethylbutylsulfonium chloride, dimethyl-$\beta$- employed in an amount of about 5 mole % of the hydrocarbyltin compound starting material.

One or more catalysts can be employed in my process at the same time. The sulfonium catalysts can be prepared by reacting a hydrocarbyl sulfide with a hydrocarbyl halide as disclosed in "Organic Chemistry of Bivalent Sulfur," by Reid, Chemical Publishing Co., Inc., N.Y.C. 1960, Volume 2, pages 66 to 72.

The isothiuronium salts can be prepared by reacting thiourea with a hydrocarbyl halide as disclosed in "Organic Chemistry of Bivalent Sulfur," by Reid, Chemical Publishing Co., Inc. N.Y.C. Volume 5, pages 27-29.

The reaction may be carried out at temperatures within the range of about 150° C. to about 250° C. A preferred range is 180° to 220° C. The reaction time can vary within the range of 0.5 to 24 hours. A preferred reaction time will range between 4 to 6 hours. The time and temperature depend on the nature of R in the hydrocarbyltin starting material and the amount of catalyst employed.

Because RSnX$_3$ may decompose at the temperature of the reaction, as represented by the equation $$RSnX_3 \rightleftharpoons RX + SnX_2 \qquad (7)$$

it is convenient to suppress this side reaction by having a small amount of RX present in the reaction vessel. R and X in equation 7 have the same identity as R and X in equations 1 to 3 above. The amount of RX required will be within the range of 1 to 10 mole percent based on the amount of tin tetrahalide charged to the reactor. Preferably the amount of RX will be about 3 mole percent of the tin tetrahalide.

If the reaction is carried out in a closed vessel, addition of RX may be unnecessary since there will be only a small loss of yield. A closed system is required only to contain materials which boil below reaction temperatures at atmospheric pressure.

In the typical practice of this invention, the hydrocarbyltin starting material and tin tetrahalide are charged to a stirring or rocking autoclave along with the appropriate catalyst. RX may also be added if desired. The system is then heated to a temperature within the range of about 180° C. to 220° C. Reaction time will be about 5 hours.

The reaction product can be used for the preparation of the corresponding tin mercaptides by reaction with the appropriate mercaptan without purification of the hydrocarbyltin trihalide or removal of the catalyst. Typically, the reaction product will assay 97 to 99% pure without purification procedures.

If desired the products can be purified by recrystallization from solvents or by distillation.

The best mode of practicing my invention will be apparent from a consideration of the following examples.

EXAMPLE 1

Into a rocking autoclave were placed 35.15 g (0.16 mole) of dimethyltin dichloride, 41.07 g (0.16 mole) of stannic chloride, 2.60 g (0.012 mole) of trimethylsulfonium iodide, and 1.5 g of methyl chloride. The mixture was heated to 200° C. and held at this temperature for 5 hours. The reaction mixture was cooled to room temperature and methylene chloride (approx. 1 pint) was added to the contents of the autoclave. The insolubles were filtered off and the filtrate concentrated to yield 65.0 g (85% yield) of crude methyltin trichloride, m.p.=45°–49°. Recrystallization from petroleum ether (b.p.=38°–45°) gave the pure product, m.p.=47.5°–49.5°.

Anal. Calcd. for $CH_3Cl_3Sn$: C, 5.00; H, 1.26; Cl, 44.30; Sn, 49.4. Found: C, 5.21; H, 1.34; Cl, 43.0; Sn, 48.9.

EXAMPLE 2

The procedure outlined in Example 1 was followed except that trimethylsulfonium chloride (28.2 g, 0.25 mole) was used in place of trimethylsulfonium iodide. From 549.2 g (2.5 mole) of dimethyltin dichloride, 651.3 g (2.5 mole) of stannic chloride and 37.9 g (0.75 mole) of methyl chloride there was obtained 1225 g (99.7% yield) of methyltin trichloride.

EXAMPLE 3

Following the procedure outlined in Example 2, except that S-butylisothiuronium iodide (1.95 g, 0.0075 mole) was used in place of trimethylsulfonium chloride, there was obtained 41.9 g (58% yield) of methyltin trichloride.

EXAMPLE 4

Following the procedure outlined in Example 3, except that S-ethylisothiuronium iodide (1.74 g, 0.0075 mole) was used in place of S-butylisothiuronium iodide, there was obtained 42.46 g (59% yield) of methyltin trichloride.

EXAMPLE 5

Following the procedure outlined in Example 1, except that di-n-butyltin dichloride is used in place of dimethyltin dichloride and n-butyl chloride in place of methyl chloride, there is obtained butyltin trichloride.

EXAMPLE 6

Following the procedure outlined in Example 1, except that di-n-butyltin dichloride is used in place of dimethyltin dichloride, n-butyl chloride in place of methyl chloride, and S-methylisothiuronium iodide in place of trimethylsulfonium iodide, there is obtained n-butyltin trichloride.

EXAMPLE 7

Following the procedure outlined in Example 1, except that di-n-octyltin dichloride is used in place of dimethyltin dichloride, n-octyl chloride in place of methyl chloride, and tetramethylenemethylsulfonium iodide in place of trimethylsulfonium iodide, there is obtained n-octyltin trichloride.

EXAMPLE 8

Following the procedure outlined in Example 1, except that di-n-octyltin dichloride is used in place of dimethyltin dichloride, n-octyl chloride in place of methyl chloride, and trimethylsulfonium chloride in place of trimethylsulfonium iodide, there is obtained n-octyltin trichloride.

It should be realized that the sulfonium and isothiuronium salts of this invention need not be added as such but can be formed in situ from the organic sulfides, thiourea, or substituted thioureas, and the corresponding organic halides, etc., under the conditions of the reaction.

The products of my invention are useful as intermediates for the preparation of stabilizers for halogenated resins such as polyvinyl chloride. For example, the hydrocarbyltin trihalides are reacted with mercaptans to produce the corresponding organotin mercaptide stabilizer. See "Encyclopedia of PVC," Vol. 1 Mercel Dekker Inc. N.Y.C. pages 295–384.

I claim:

1. The process of preparing monohydrocarbyltin trihalide by reacting $SnX_4$ with a member of the group consisting of $R_4Sn$, $R_3SnX$, and $R_2SnX_2$ in quantities substantially as shown in the equations $R_4Sn+3SnX_4\rightarrow 4RSnX_3$, $R_3SnX+2SnX_4\rightarrow 3RSnX_3$, $R_2SnX_2+SnX_4\rightarrow 2RSnX_3$, while at a temperature within the range of about 150° C. to 250° C., and in the presence of one or more sulfonium or isothiuronium catalysts selected from the group consisting of the following:

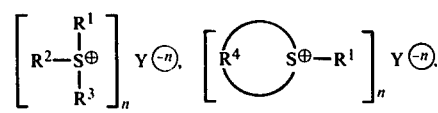

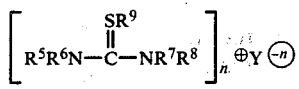

wherein: X is bromide, chloride and iodide; R, $R^1$, $R^2$, $R^3$, $R^5$, $R^6$, $R^7$, $R^8$ and $R^9$ are hydrocarbyl radicals, of 1–24 carbon atoms; $R^5$, $R^6$, $R^7$, and $R^8$ can also be hydrogen; $R^4$ is a hydrocarbon linking group of 3–5 carbon atoms; n is the valence of the anion Y; and, Y is an anion.

2. The process of claim 1 in which the temperature ranges from about 180° C. to 220° C.

3. The process of claim 1 conducted in a closed reaction vessel.

4. The process of claim 1 carried out in the presence of a small amount of RX where R and X are defined as in claim 1.

5. The process of claim 1 in which X is chloride.

6. The process of claim 5 in which the catalyst is trimethyl sulfonium chloride.

7. The process of claim 1 in which the catalyst is present at a minimum concentration of at least 0.001 moles per mole of $SnX_4$.

8. The process of claim 1 in which Y is selected from the group consisting of $Cl^{-1}$, $Br^{-1}$, $I^{-1}$, $SO_4^{-2}$, $CH_3SO_4^{-1}$, p-$CH_3C_6H_4SO_3^{-1}$, p-$BrC_6H_4SO_3^{-1}$, $PO_4^{-3}$, $NO_3^{-1}$, $CH_3CO_2^{-1}$, $SnCl_3^{-1}$, $SnBr_3^{-1}$, and $SnI_3^{-1}$.

9. The process in claim 1 in which $R^1$, $R^2$, $R^3$, $R^5$, $R^6$, $R^7$, $R^8$ and $R^9$ are substituted with one or more inert substituents selected from the group consisting of alcohol, ether, ester and halide.

* * * * *